United States Patent
Chalupova et al.

(10) Patent No.: US 12,404,256 B2
(45) Date of Patent: Sep. 2, 2025

(54) PROCESS FOR PREPARING OZANIMOD

(71) Applicant: Synthon B.V., Nijmegen (NL)

(72) Inventors: Lenka Chalupova, Blansko (CZ); Marian Buchlovic, Blansko (CZ)

(73) Assignee: Synthon B.V., Nijmegen (NL)

( * ) Notice: Subject to any disclaimer, the term of this patent is extended or adjusted under 35 U.S.C. 154(b) by 862 days.

(21) Appl. No.: 17/627,386

(22) PCT Filed: Jul. 16, 2020

(86) PCT No.: PCT/EP2020/070188
§ 371 (c)(1),
(2) Date: Jan. 14, 2022

(87) PCT Pub. No.: WO2021/009306
PCT Pub. Date: Jan. 21, 2021

(65) Prior Publication Data
US 2022/0259163 A1     Aug. 18, 2022

(30) Foreign Application Priority Data
Jul. 16, 2019   (EP) ..................................... 19186630

(51) Int. Cl.
*C07D 271/06*    (2006.01)

(52) U.S. Cl.
CPC .................................. *C07D 271/06* (2013.01)

(58) Field of Classification Search
CPC .................................................... C07D 271/06
See application file for complete search history.

(56) References Cited

FOREIGN PATENT DOCUMENTS

| | | |
|---|---|---|
| CN | 108727291 | 11/2018 |
| IN | 201741033697 | 3/2019 |
| WO | WO 2011/060392 | 5/2011 |
| WO | WO 2017/215617 | 12/2017 |
| WO | WO 2018/033149 | 2/2018 |
| WO | WO 2018/184185 | 10/2018 |
| WO | WO 2018/215807 | 11/2018 |
| WO | WO 2020115200 | 6/2020 |

*Primary Examiner* — Shawquia Jackson
(74) *Attorney, Agent, or Firm* — Buscher Patent PLLC

(57) ABSTRACT

The present invention relates to the process of preparation of compound of formula (I) or a salt thereof. Further it relates to the solid form of compound (I).

20 Claims, 1 Drawing Sheet

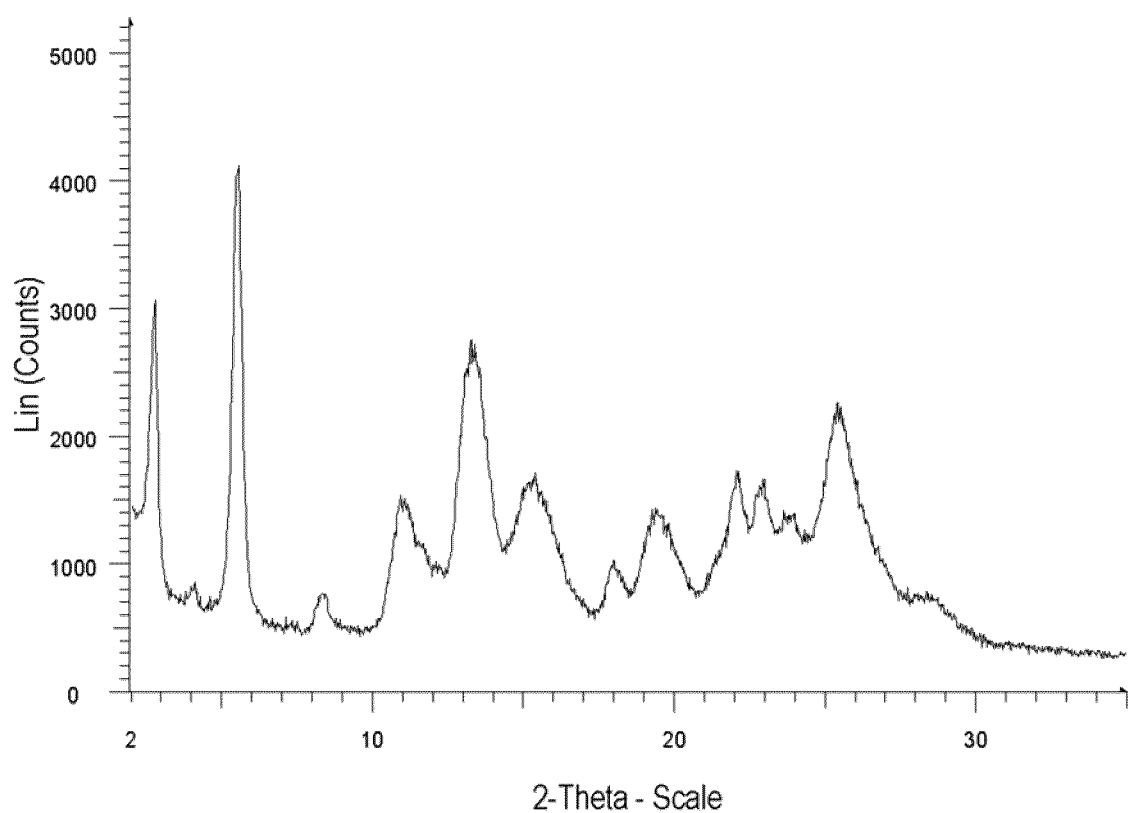

PROCESS FOR PREPARING OZANIMOD

BACKGROUND OF THE PRESENT INVENTION

This invention relates to a process of preparation of solid form of ozanimod, the compound of formula (1):

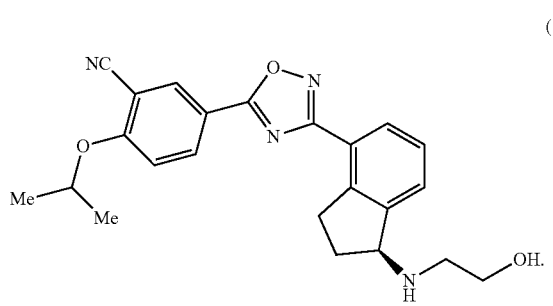

Ozanimod, 5-[3-[1(S)-(2-Hydroxyethylamino)-2,3-dihydro-1H-inden-4-yl]-1,2,4-oxadiazol-5-yl]-2-isopropoxybenzonitrile, is an oral agonist of the lysophospholipid S1P1 and S1P5 receptors. Ozanimod is in phase III clinical development for the treatment of ulcerative colitis and for the treatment of Crohn's disease and is also awaiting registration in USA and Europe for the treatment for patients with relapsing multiple sclerosis.

Ozanimod was first disclosed in WO 2011/060392 application. The application also describes a process for preparation of ozanimod. Final product is purified by column chromatography or preparative HPLC. Chromatographic purification steps are tedious and expensive process steps on an industrial scale. Therefore, there is a need for alternative process that does not comprise chromatographic purification and provides ozanimod in sufficient purity and yield.

Several crystalline forms of ozanimod and their preparations were disclosed in WO 2017/215617, WO 2018/033149 by Crystal Pharmaceutical Co., WO 2018/184185 by SoliPharma LCC or WO 2018/215807 by Egis Gyogyszergyar Zrt. These applications include the procedures which were used for synthesis of small development samples and are described in general way. Therefore, there is a need for a scalable purification process suitable for industrial scale.

It was surprisingly discovered that ozanimod or pharmaceutically acceptable salt thereof can be prepared according to following scheme:

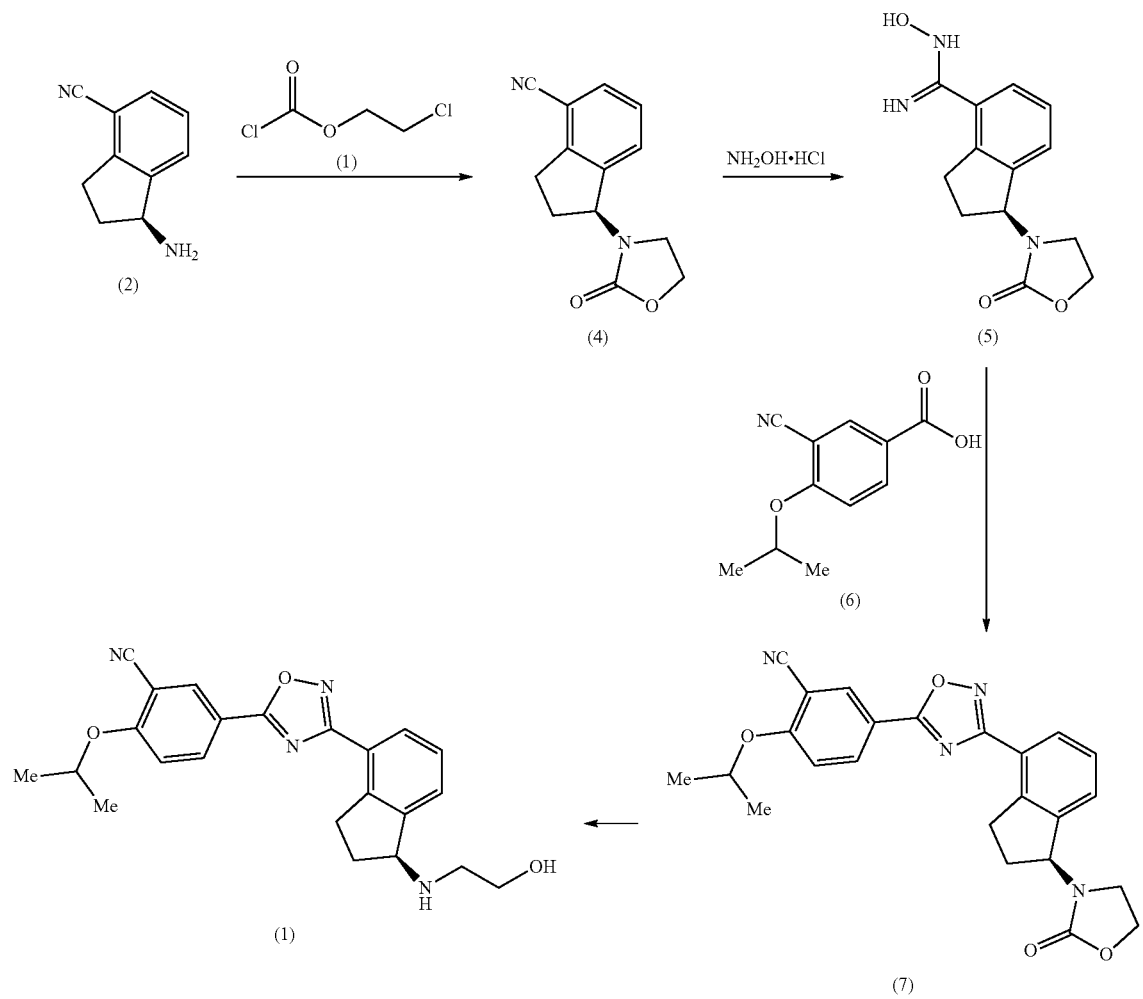

The present application focuses on the last step of the process.

BRIEF DESCRIPTION OF THE INVENTION

The present invention relates to a process for preparation of solid form of a compound of formula (1),

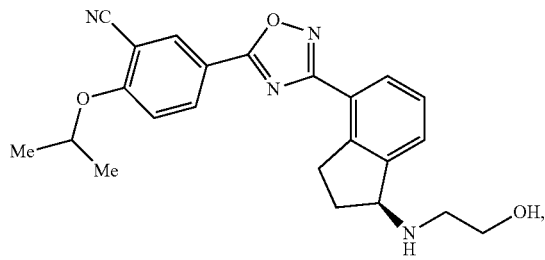

(1)

comprising:
I. Reacting compound (7) in a presence of a compound of formula (R)$_3$SiOM,
where R is selected from C$_1$-C$_5$ alkyl or aryl and M is selected from Na, K or Li, in a solvent to provide compound (1);

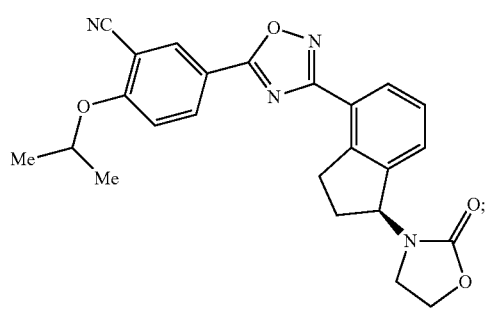

(7)

II. Addition of an acid or silicagel;
III. Isolation of compound (I) from alkyl acetate or an alcohol or a mixture thereof;
IV. Optional salification of a compound (I).

The presented process does not comprise chromatographic purification and provides ozanimod or a salt thereof in good purity and yield.

The present invention further relates to a solid form of ozanimod obtained by crystallization of ozanimod from alkyl acetate or an alcohol or a mixture of alkyl acetate and alcohol.

BRIEF DESCRIPTION OF THE DRAWINGS

FIG. 1 depicts the X-Ray Powder Diffractogram (XRPD) of ozanimod free base obtainable according to the Example 2 or 3.

DETAILED DESCRIPTION OF THE INVENTION

The present invention relates to a process for preparation of compound of formula (1) or a salt thereof,

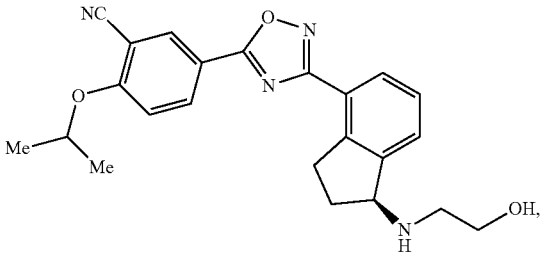

(1)

comprising:
I. Reacting compound (7) in a presence of a compound of formula (R)$_3$SiOM,
where R is selected from C$_1$-C$_5$ alkyl or aryl and M is selected from Na, K or Li, in a solvent to provide compound (1);

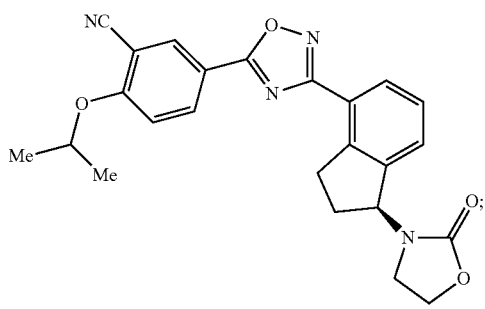

(7)

II. Addition of an acid or silicagel;
III. Isolation of compound (I) from alkyl acetate or an alcohol or a mixture thereof;
IV. Optional salification of a compound (I).

Compound (7) is transformed into compound (1) in a presence of a compound of formula (R)$_3$SiOM, where R is selected from C$_1$-C$_5$ alkyl or aryl and M is selected from Na or K or Li in a solvent to provide compound (1). As a solvent for example tetrahydrofurane or 2-methyl tetrahydrofurane or dioxane or dimethylformamide or dimethylacetamide or dimethylsulfoxide or a mixture thereof, preferably tetrahydrofurane can be used. The compound of formula (R)$_3$SiOM, R is selected from C$_1$-C$_5$ alkyl or aryl and M is selected from Na or K or Li, is preferably selected from (R)$_3$SiONa or (R)$_3$SiOK. More preferably it is sodium or potassium trimethylsilinoate of formula:

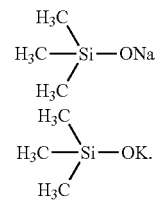

Advantageously compound of formula (R)$_3$SiOH, R is selected from C$_1$-C$_5$ alkyl or aryl is added into the mixture. Preferably it is trialkylsilanol, more preferably trimethylsilanol. The ratio (vol:vol) between the solvent and the compound of formula (R)₃SiOH can be between 2:1 and 6:1, preferably it is between 3:1 and 5:1.

The concentration of compound (7) in the solvent can be between 0.04 g/ml and 0.3 g/ml, preferably it is between 0.04 g/ml and 0.06 g/ml. The molar ratio between compound (7) and the compound of formula (R)₃SiOM can be between 1:2 and 1:6, preferably it is between 1:3 and 1:5. The reaction mixture is stirred at a temperature between 50° C. and the reflux temperature of the used solvent for between 0.5 and 10 hours, preferably for between 1 and 3 hours.

The acid added in step II is preferably weak acid selected from formic acid, acetic acid, propionic acid, butyric acid, citric acid, benzoic acid or lactic acid, preferably acetic acid.

The isolation of compound of formula (I) can be performed from alkyl acetate or an alcohol or a mixture thereof. The compound of formula (I) can be extracted with alkyl acetate or a mixture of alkyl acetate and alcohol. The alkyl acetate can be for example methyl acetate, ethyl acetate, isopropyl acetate or n-Butyl acetate (n-BuOAc). The alcohol can be for example methanol, ethanol, propanol, isopropanol, butanol, tert-butanol or mixtures thereof. The ratio (vol:vol) between the reaction mixture and alkyl acetate or a mixture of alkyl acetate and alcohol can be between 2:1 and 1:1. The phases were separated and the organic phase was then stirred and preferably filtered. The filtrate can be heated back to temperature between 50° C. and the reflux temperature of the used solvent. The organic phase is separated and the water phase is extracted at the same temperature with additional portion of alkyl acetate or a mixture of alkyl acetate and alcohol. The extract is preferably concentrated under vacuum to around half of the volume.

Alternatively, the solvent can be switched to alcohol by addition of an alcohol and vacuum distillation.

The mixture can be treated with active and filtrated.

The mixture is then cooled to the temperature between −10° C. and 10° C., preferably to the temperature between 0 and 5° C., stirred for 15 minutes to 2 hours, more preferably 20 minutes to 1 hour and filtered. The filtration cake is washed with cold alkyl acetate or a cold alcohol or a mixture thereof. The obtained solid can be dried. Alternatively, the antisolvent can be added to the mixture. The antisolvent can be for example an alkane, an ether, acetone or toluene.

Compound (I) prepared according to this invention is a solid form and can be characterized by XRPD pattern having peaks at 5.6°, 10.9°, 18.0° and 25.6° degrees 2-theta±0.2 degrees 2-theta. The solid form of compound (I) according to this invention can be further characterized by XRPD pattern having peaks at 2.7°, 5.6°, 10.9°, 18.0°, 22.1°, 22.8° and 25.6° degrees 2-theta±0.2 degrees 2-theta. The solid form of compound (I) according to this invention can be also characterized by the reflections presented in Table 1.

TABLE 1

| Angle 2-Theta ° | Intensity % |
| --- | --- |
| 2.7 | 47.4 |
| 5.6 | 100.0 |
| 8.5 | 25.2 |
| 10.9 | 29.2 |
| 11.3 | 34.0 |
| 13.3 | 51.7 |
| 15.1 | 30.6 |
| 17.0 | 17.6 |
| 18.0 | 18.9 |

TABLE 1-continued

| Angle 2-Theta ° | Intensity % |
| --- | --- |
| 19.5 | 27.1 |
| 22.1 | 28.9 |
| 22.8 | 28.9 |
| 23.6 | 25.9 |
| 25.6 | 38.3 |
| 28.7 | 13.4 |
| 31.7 | 17.5 |

The solid form of compound (1) prepared according to this invention can also be characterized by XRPD pattern depicted in FIG. 1.

Compound (1) prepared according to process of the invention can be transformed to a salt with sulfuric acid, citric acid, formic acid, benzoic acid, acetic acid, oxalic acid, $H_3PO_4$ or HCl, preferably hydrochloric acid. The salt can be prepared by contacting ozanimod (compound (1)) with the corresponding acid in a solvent comprising an alcohol (such as isopropanol, methanol, ethanol, propanol, butanol or tert-butanol), 2-methyl tetrahydrofurane, tetrahydrofurane (THF), water or a mixture thereof, heating the mixture at a temperature between 70° C. and the reflux temperature of used solvent and subsequent cooling of the mixture to a temperature between 0° C. and 25° C., preferably at a temperature between 20 and 25° C. and stirring at this temperature for between 1 and 10 hours, preferably between 1 and 3 hours, to obtain a crystalline form of ozanimod salt with the corresponding acid. The concentration of ozanimod in the solvent can be between 0.01 and 0.1 g/ml, preferably it is between 0.03 and 0.05 g/ml. The molar ratio between ozanimod and the acid can be between 1:1 and 1:5, preferably it is between 1:1.05 and 1:2. The isolated ozanimod salt can be separated by any suitable technique, for example by filtration or using a centrifuge.

The invention will be further described with reference to the following examples:

EXAMPLES

XRPD spectrum was obtained using the following measurement conditions:

Panalytical Empyrean diffractometer with Θ/2Θ geometry (transmition mode), equipped with a PixCell 3D detector:

| | |
| --- | --- |
| Start angle (2Θ): | 2.0° |
| End angle (2Θ): | 35.0° |
| Step size: | 0.026° |
| Scan speed: | 0.0955 °/seconds |
| Radiation type: | Cu |
| Radiation wavelengths: | 1.5406Å (Kα1), primary monochromator used |
| Divergence slit: | 1/2° |
| Antiscatter slit: | 1/2° |
| Soller slit: | 0.02 rad |
| Detector slit: | 7.5 mm |
| Rotation speed: | 30 rpm |

Example 1

Preparation of 5-[3-[1(S)-(2-Hydroxyethylamino)-2,3-dihydro-1H-inden-4-yl]-1,2,4-oxadiazol-5-yl]-2-isopropoxybenzonitrile (Ozanimod Free Base)

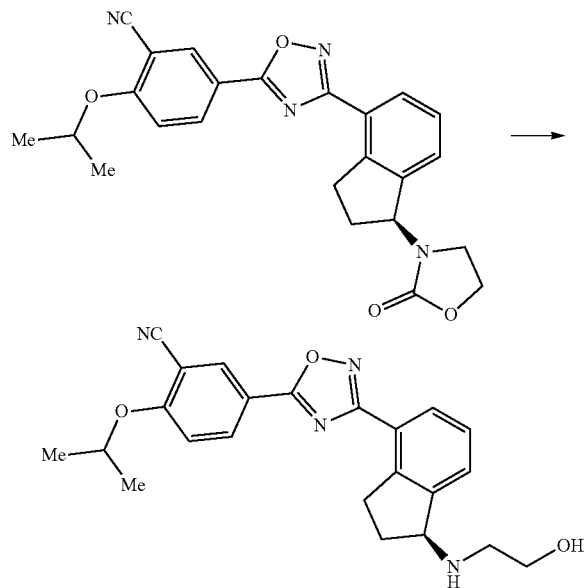

5 g of (S)-2-isopropoxy-5-(3-(1-(2-oxooxazolidin-3-yl)-2,3-dihydro-1H-inden-4-yl)-1,2,4-oxadiazol-5-yl)benzonitrile was dissolved in 32.6 ml of 2-methyltetrahydrofuran, followed by addition of 12.9 ml of trimethylsilanol and 17.4 ml of solution of potassium trimethylsilanoate in tetrahydrofurane (THF) (2 mol/l solution). The mixture was heated at 60° C. and stirred at this temperature for one hour. Afterwards, 50 ml of water, 2 ml of acetic acid and 50 ml of nBuOAc were added. The mixture was stirred for 5 min. and filtered. The filtrate was heated back to 70° C. and organic phase was separated. Water phase was extracted with additional 50 ml of nBuOAc at 70° C. Combined organic phases were heated back to 70° C. and concentrated to half of volume.

Example 2

Crystallization of Ozanimod Free Base from nBuOAc

The extract prepared in example 1 was heated to 70° C., then cooled to 0-5° C., stirred for 30 min and filtered. The filtration cake was washed with 10 ml of cold nBuOAc. The material was dried at room temperature overnight to give off-white solid (3.7 g, 78% of the theoretical yield, HPLC purity 93.2%). XRPD pattern of obtained solid is depicted in FIG. 1.

Example 3

Crystallization of Ozanimod Free Base from nBuOAc and Carbofiltration

The extract prepared in example 1 was heated to 70° C., followed by addition of charcoal (0.5 g), stirred at the same temperature for 15 min. Charcoal was filtered off and then the mixture was cooled to 0-5° C., stirred for 30 min and filtered. The filtration cake was washed with 10 ml of cold nBuOAc. The material was dried at room temperature overnight to give off-white solid (3.0 g, 64% of the theoretical yield, HPLC purity 95.2%).

Example 4

Preparation of Ozanimod Free Base 15.6 g of potassium tert-butoxide was charged into 500 ml reactor and was dissolved in 200 ml of THF. 66.9 ml of trimethylsilanol was added slowly, the temperature of the mixture was controlled below 30° C. The mixture was stirred for 5 min. at room temperature. Afterwards, 20.0 g of (S)-2-isopropoxy-5-(3-(1-(2-oxooxazolidin-3-yl)-2,3-dihydro-1H-inden-4-yl)-1,2,4-oxadiazol-5-yl)benzonitrile was added. The mixture was stirred at 60° C. for 90 minutes. 30 g of silicagel and 4 g of charcoal were added, the mixture was stirred at 60° C. for 30 minutes, filtered to remove adsorbents. The filtrate was heated to 50° C. and concentrated in vacuum to approximate volume 50 ml. The solvent was then switched to methanol by addition of 400 ml of methanol and vacuum distillation to a final volume 300 ml. The formed solid was then dissolved at 50° C. 8 g of charcoal was added, the mixture was stirred at 50° C. for 30 minutes, filtered to remove adsorbents. The filtrate was heated to 50° C., the mixture was cooled to 0-5° C., stirred for 30 min. and filtered. The filtration cake was washed with cold methanol (2×50 ml). The material was dried at room temperature overnight to give off-white solid (10.7 g, 57% of the theoretical yield, HPLC purity 97.8%).

The invention claimed is:

1. A process for preparation of a compound of formula (1) or a salt thereof, (1)

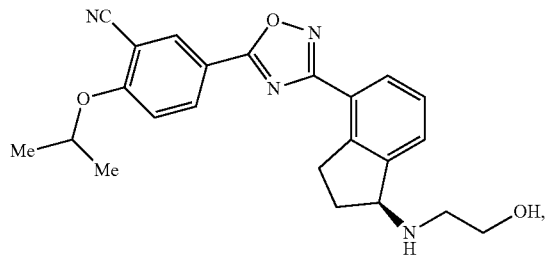

comprising:
  i) reacting a compound of formula (7) in a presence of a compound of formula (R)$_3$SiOM, where R is selected from C$_1$-C$_5$ alkyl or aryl and M is selected from Na or K or Li, in a solvent at a temperature between 50° C. and reflux temperature of the solvent to provide the compound of formula (1) in a reaction mixture;

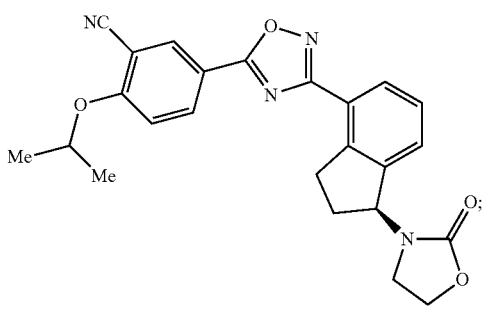

(7)

ii) adding an acid or silicagel to said reaction mixture;
iii) isolating a solid form of the compound of formula (1) from alkyl acetate or an alcohol or a mixture thereof; and
iv) optionally salifying the compound of formula (1).

2. The process according to claim 1 wherein the compound of formula $(R)_3SiOM$ used in step i) is selected from the group consisting of $(R)3SiONa$ and $(R)3SiOK$.

3. The process according to claim 2 wherein the compound of formula $(R)_3SiOM$ is sodium or potassium trimethylsilinoate.

4. The process according to claim 1 wherein the solvent used in step i) is selected from the group consisting of tetrahydrofurane, methyl tetrahydrofurane, dioxane, dimethoxyethane and anisol.

5. The process according to claim 1 wherein the step i) is performed in a presence of a compound of formula $(R)_3SiOH$, R is selected from the group consisting of C1-C5 alkyl and aryl.

6. The process according to claim 5 wherein the compound of formula $(R)_3SiOH$ is selected from $(C_1-C_5$ alkyl$)_3SiOH$.

7. The process according to claim 6 wherein the compound of formula $(R)_3SiOH$ is $(CH_3)_3SiOH$.

8. The process according to claim 1 wherein the acid added in step ii) is selected from the group consisting of formic acid, acetic acid, propionic acid, butyric acid, citric acid, benzoic acid and lactic acid.

9. The process according to claim 8 wherein the acid is acetic acid.

10. The process according to claim 1 wherein the alkyl acetate in step iii) is selected from the group consisting of methyl acetate, ethyl acetate, isopropyl acetate and n-butyl acetate.

11. The process according to claim 1 wherein the alcohol in step iii) is selected from the group consisting of isopropanol, methanol, ethanol, propanol, butanol and tert-butanol.

12. The process according to claim 1 wherein the isolating in step iii) is performed by (a) switching the solvent in the reaction mixture to an alcohol and then (b) cooling the mixture or adding an antisolvent.

13. The process according to claim 12 wherein the mixture is cooled to a temperature between −10° C. and 10° C.

14. A solid form of compound of formula (1)

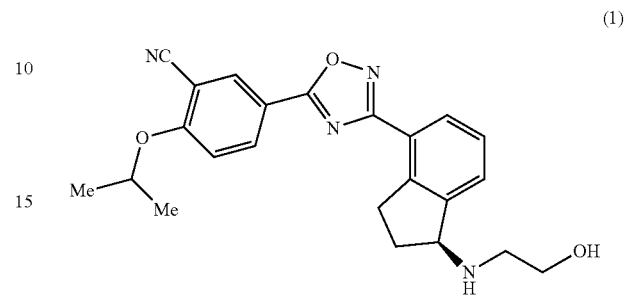

(1)

characterized by XRPD pattern having peaks at 5.6°, 10.9°, 18.0° and 25.6° degrees 2-theta±0.2 degrees 2-theta.

15. A solid form of compound of formula (1)

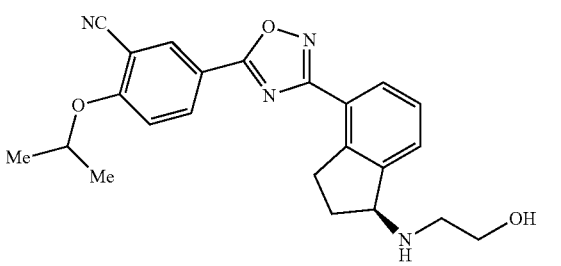

(1)

characterized by XRPD pattern of FIG. 1.

16. The process according to claim 1, wherein said isolated solid form of the compound of formula (1) is salified to form a pharmaceutically acceptable salt thereof.

17. The process according to claim 16, wherein said salification of the compound of formula (1) produces ozanimod hydrochloride.

18. The process according to claim 16, which further comprises isolating said salt of the compound of formula (I).

19. The process according to claim 17, which further comprises isolating said ozanimod hydrochloride.

20. The process according to claim 1, wherein said isolating in step iii) comprises crystallization of the compound of formula (1).

* * * * *